United States Patent [19]

Loo

[11] Patent Number: 4,930,220

[45] Date of Patent: Jun. 5, 1990

[54] SCALPEL BLADE HOLDER

[76] Inventor: George D. H. Loo, 9814 Curwood Pl., Beverly Hills, Calif. 90210

[21] Appl. No.: 330,226

[22] Filed: Mar. 29, 1989

[51] Int. Cl.⁵ .............................................. B26B 1/00
[52] U.S. Cl. ..................................................... 30/339
[58] Field of Search ................. 30/335, 339, 338, 337, 30/329; 128/305, 304, 751

[56] References Cited

U.S. PATENT DOCUMENTS

| | | | |
|---|---|---|---|
| 2,109,108 | 2/1938 | Fesler | 30/337 |
| 2,316,985 | 4/1943 | Niedermayer | 30/335 |
| 2,877,553 | 3/1959 | Matwijcow | 30/339 |
| 2,960,769 | 11/1960 | Matwijcow | 30/340 |
| 3,412,467 | 11/1968 | Matwijcow | 30/339 |
| 3,672,054 | 6/1972 | Kaufman | 30/339 X |
| 3,845,554 | 11/1974 | Joanis et al. | 30/125 |
| 4,292,738 | 10/1981 | Osada | 30/162 |
| 4,617,738 | 10/1986 | Kopacz | 30/330 |
| 4,798,000 | 1/1989 | Bedner et al. | 30/339 |

Primary Examiner—Frank T. Yost
Assistant Examiner—Willmon Fridie, Jr.
Attorney, Agent, or Firm—Limbach, Limbach & Sutton

[57] ABSTRACT

In this invention, an improved scalpel blade holder for holding a conventional scalpel blade is disclosed. The conventional scalpel blade has two elongated holes that are coextensive with one another. Each of the holes has a length and a width with the holes being attached to one another in the length direction and the hole near the blade portion having a width smaller than the hole away from the blade portion. The blade holder has an elongated handle member having a distal end and a proximal end along the length. A support member is near the distal end. The support member has a groove along the periphery parallel to the length direction. The width of the support member between the groove is substantially equal to the width of the smaller hole of the blade. The length of the support member is less than the sum of the lengths of the two holes in the blade. A slidable member is also in the handle positioned spaced apart from the support member such that the distance from the proximal end of the slidable member to the groove at the distal end of the support member is substantially the same as the sum of the two lengths of the two holes in the blade. The slidable member is movable in the thickness direction and a means for locking the slidable member between the first position whereby the member is above the plane of the groove, and in a second position whereby the slidable member is just below the plane of the groove is also disclosed.

6 Claims, 2 Drawing Sheets

4,930,220

SCALPEL BLADE HOLDER

TECHNICAL FIELD

The present invention relates to a scalpel blade holder and more particularly to an improved blade holder wherein the attachment and removal of a conventional scalpel blade can be accomplished with great ease and safety.

BACKGROUND OF THE INVENTION

Detachable scalpel blades or knives for use with holders are well known in the art. See, for example, U.S. Pat. Nos. 2,109,108; 2,316,985; 2,960,769; 3,845,554; 4,292,738; and 3,412,467.

A number of the foregoing references discloses a rod which can be slid into and out of a circular hole in a surgical blade. See, for example, U.S. Pat. No. 2,316,985. However, none of the references cited heretofore discloses or refers to a scalpel blade holder that can accept a conventional scalpel blade, which does not have simply a circular hole into and out which a rod can move.

SUMMARY OF THE INVENTION

In the present invention a scalpel blade holder for holding a conventional scalpel blade is disclosed. The conventional scalpel blade has a blade portion near the anterior thereof and a blunt portion near the posterior thereof. The blade has a substantially elongated first hole near the blunt portion with the first hole having a first length and a first width with the first length being parallel to the direction from the anterior to the posterior. A substantially elongated second hole anterior to and coextensive with the first hole is also in the blade. The second hole has a second length parallel to and collinear with the first length and a second width smaller than the first width of the first hole.

The improved scalpel blade holder of the present invention comprises an elongated handle member having a length, a width and a thickness with a distal end and a proximal end along the length direction. An elongated support member is positioned near the distal end. The support member has a groove along its periphery parallel to the length direction wherein the width of the support member between the groove is substantially equal to the second width of the second hole of the blade. The length of the support member is less than the sum of the first and second lengths of the first and second holes of the scalpel blades. A slidable member is positioned spaced apart from the support member in the handle member. The slidable member is movable along the thickness direction and has a width substantially equal to the first width of the first hole of the scalpel blade. The slidable member is positioned such that the distance from the proximal end of the slidable member to the groove at the distal end of the support member is substantially the same as the sum of the first and second lengths of the first and second holes of the scalpel blade. A means for locking the slidable member along the thickness direction between the first position and a second position is also provided. In the first position, the slidable member is above the plane of the groove. In the second position, the slidable member is just below the plane of the groove.

BRIEF DESCRIPTION OF THE DRAWINGS

FIG. 2b is a side view of the prior art scalpel blade holder shown in FIG. 2a.

DETAILED DESCRIPTION OF THE DRAWINGS

Figure 1:
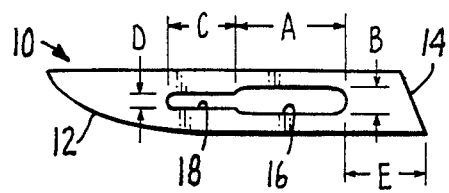
FIG. 1 is a top plan view of a conventional scalpel blade which is attachable to the improved scalpel blade holder of the present invention.

Referring to FIG. 1 there is shown a top plan view of a conventional scalpel blade 10 which can be used with the improved scalpel blade holder 30 of the present invention. The scalpel blade 10 has a blade portion 12 near the anterior thereof and a blunt portion 14 near the posterior thereof. The blade 10 has a substantially elongated first hole 16 near the blunt portion 14 of the scalpel blade 10. The first hole 16 has a first length A and a first width B with the first length A being parallel to the direction from the anterior 12 to the posterior 14. The blade 10 also has a substantially elongated second hole 18 anterior to and coextensive with the first hole 16. The second hole 18 has a second length C which is parallel to and collinear with the first length A. The second hole 18 also has a second width D smaller than the first width B.

Figure 2A:
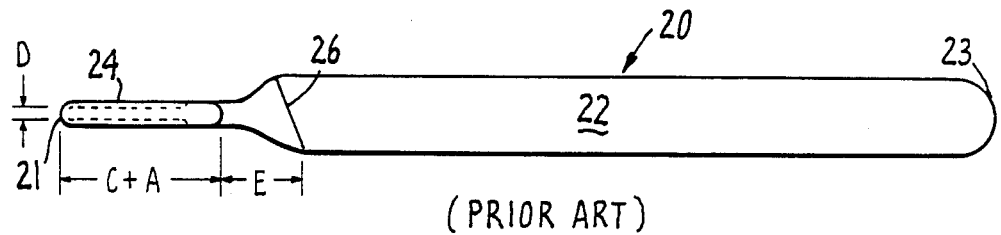
FIG. 2a is a top plan view of a scalpel blade holder of the prior art suitable for holding the scalpel blade shown in FIG. 1.
Figure 2B:
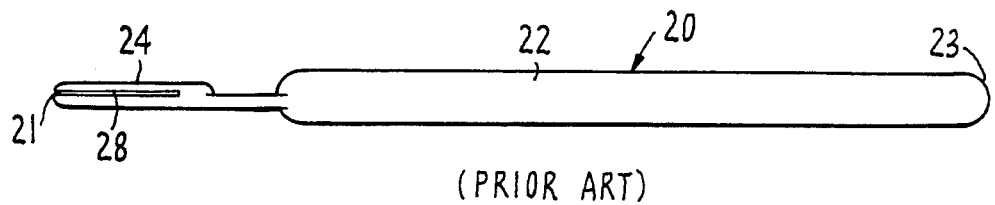

Referring to FIG. 2a there is shown a top plan view of a scalpel blade holder 20 of the prior art. The scalpel blade holder 20 of the prior art comprises an elongated handle member 22 having a length, a width, and a thickness with the member 20 having a distal end 21 and a proximal end 23 along the length. An elongated support member 24 is substantially near the distal end 21 of the handle member 22. The support member 24 has a groove 28 along its periphery parallel to the length direction from the proximal end 23 to the distal end 21. The support member 24 has a length which is substantially equal to the sum of the lengths (C+A) of the second hole 18 and of the first hole 16 of the surgical blade 10. The width of the support member 24 between the groove 28 is substantially equal to the second width D of the second hole 18 of the surgical blade 10. Finally, a step 26 is provided at a distance E which is spaced apart from the proximal end of the support member 24. The distance E is substantially equal to the distance of separation of the posterior end of the first hole 16 from the blunt portion 14 of the scalpel blade 10.

The typical dimensions of the scalpel blade holder 20 of the prior art is the support member 24 being approximately 18 millimeters in length and 2 millimeters wide. The height of the support member 24 is approximately 2 millimeters. The groove on the two sides of the support member 24 separates the support member 24 into two parts, each being approximately 1 millimeter thick, but with the upper part thinner than the lower part. The groove is about one half millimeter wide and one half millimeter deep. The grooves are approximately 13 millimeters long and start at the distal end on each side on the 18 millimeter long support member 24.

In the operation of the scalpel blade 20 of the prior art, the elongated support member 24 is slipped through the first hole 16 of the scalpel. blade 10 and into the second hole 18 such that the edge of the hole 18 slides into the groove 28 of the scalpel blade holder 20. Since the blade 10 is made of a flexible, springy steel-like material, the blade is bent over the support member 24 and then snapped over the support member 24 until the blunt portion 14 rests against the stop 26. Once the blade 10 has been attached on the handle 20, the grooves 28 keep the blade 10 from moving in the thickness direction. Since the length of the support member 24 is approximately the same as the sum of the lengths (A+C) of the first and second holes 16 and 18 respectively, the ends of the support member 24 keep the blade 10 from moving in the length direction. Finally, the grooves 28 and the stop 26 keep the blade 10 from moving in the width direction during use.

To remove the surgical blade 10 from the handle 20 of the prior art, the reverse operation must be performed. The blunt portion 14 of the blade 10 must be pushed distally from the stop 26 and must be bent simultaneously upwards to lift over the proximal end of the support member 24. The handle 20 with the support 24 must then be slid out from the second hole 18. Such a procedure is difficult and often the health care worker is exposed to self-inflicted accidental wounds. With the concern over infectious diseases of patients, such accidents can be of great concern to health care workers.

Figure 3A:
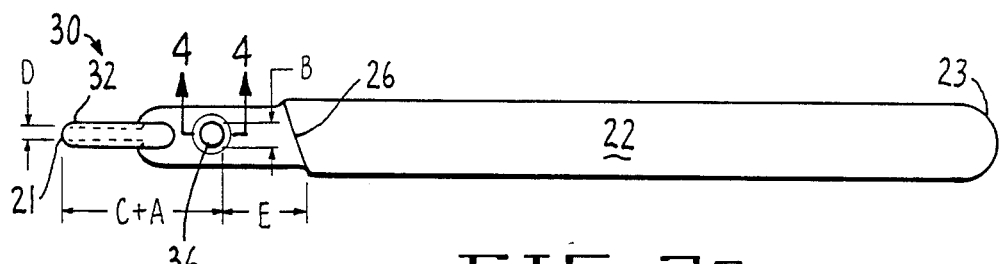
FIG. 3a is a top plan view of an improved scalpel blade holder of the present invention suitable for holding the scalpel blade shown in FIG. 1.
Figure 3B:
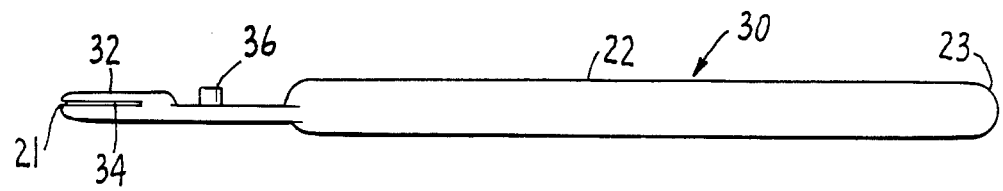
FIG. 3b is a side view of the improved scalpel blade holder of the present invention.

Referring to FIG. 3a there is shown a top plan view of the improved scalpel blade holder 30 of the present invention. The improved holder 30 comprises an elongated handle member number 22 having a length, a width, and a thickness with the member 22 having a distal end 21 and a proximal end 23 along the length direction. The handle member 22 is of the same design as the prior art.

An elongated support member 32 is positioned near the distal end 21 of the handle member 22. The support member 32 has a groove 34 along its periphery, parallel to the length direction. Further, the width of the support member between the grooves is substantially equal to the second width D of the second hole 18 of the blade 10. Unlike the prior art blade holder 20, however, the length of the elongated support member 32 is less than the sum of the first and second lengths (A+C) of the first and second holes 16 and 18 respectively of the blade 10.

A slidable member 36 is positioned in the handle member 22 spaced apart from the support member 32. The slidable member 36 is positioned such that the distance from the proximal end of the slidable member 36 to the groove at the distal end of the support member 32 is substantially the same as the sum of the first and second lengths (A+C) of the first and second holes 16 and 18 respectively of the blade 10. The slidable member 36 is movable in the thickness direction and has a width which is substantially equal to the first width B of the first hole 16 of the blade 10.

A means for locking the slidable member 36 along the thickness direction between a first position and a second position is provided. In the first position, the slidable member 36 is above the plane of the groove 34, and in the second position the slidable member 36 is just below the plane of the groove 34.

Figure 4A:
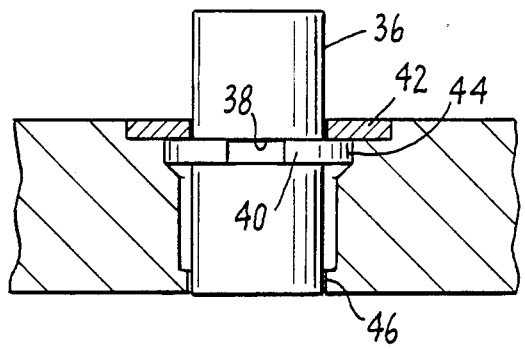
FIG. 4a is a cross-sectional view taken along the lines 4—4 shown in FIG. 3a of a portion of the improved scalpel blade holder of the present invention showing the slidable member in a locked first position.
Figure 4B:
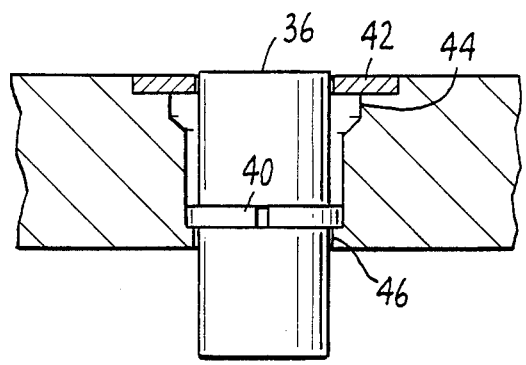
FIG. 4b shows the slidable member in an unlocked second position.
Figure 5:
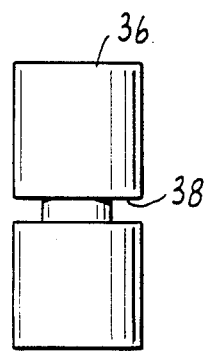
FIG. 5 is a side view of a preferred embodiment of the slidable member used in the improved scalpel blade holder of the present invention.
Figure 6:
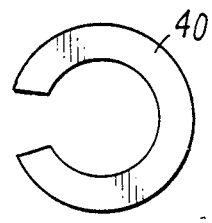
FIG. 6 is a top plan view of a locking split ring spring used in the improved scalpel blade holder of the present invention.
Figure 7:
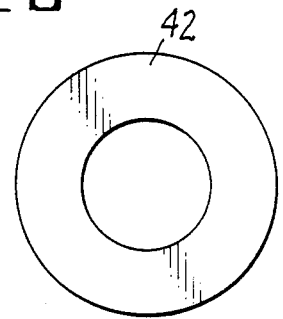
FIG. 7 is a top plan view of a retaining washer used in the improved scalpel blade holder of the present invention.

Referring to FIGS. 4a and 4b where is shown in greater detail the locking means for locking the slidable member 36 between the first position shown in FIG. 4a and the second position shown in FIG. 4b.

In one preferred embodiment, the slidable member 36 is substantially shaped in a rod. The rod 36 has a groove 38. A split compression ring 40 is placed in the groove 38 of the rod 36. The rod 36 with the split ring 40 is movable in the handle 22 in the thickness direction between a first position shown in FIG. 4a and a second position shown in FIG. 4b. In the first position, the split ring 40 expands into a groove 44 within the handle member 22, but still being retained within the groove 38 of the rod 36 thereby holding the rod 36 in the first position. A retaining washer 42 prevents the ring 40 from being pushed out of the groove 44 and out of the handle member 22. In the second position, the ring 40 is compressed into the groove 38 of the rod 36. A retaining lip 46 prevents the rod 36 from being pushed out of the handle member 22.

To attach the blade 10 to the improved blade holder 30 of the present invention, the elongated support member 32 is inserted into the second hole 18 of the blade 10 as before. The periphery of the hole 18 is slipped into the groove 34 of the elongated support member 32. Since the length of the support member 32 is less than the sum of the first and second lengths (A+C) of the first and second holes 16 and 18 respectively of the blade 10. The blade 10 does not need to flex and will automatically come to rest against the blade handle 22 and against the stop 26. The slidable member rod 36 is then moved in the thickness direction and is pushed into the first position and is locked in the first position. In this manner, the blade 10 is attached to the improved blade holder 30. The blade is prevented from moving in the thickness direction by the periphery of the second hole 18 being fixed into the groove 34. The blade 10 is prevented from moving in the width direction by the width D of the elongated support member 32 being the same size as the width of the second hole 18. Finally, the blade 10 is prevented from moving in the length direction by the combination of the elongated support member 32 and the slidable member 36 being positioned such that the distance from the distal end of the groove of the elongated support member 32 to the proximal end of the slidable member 36 being equal to the sum of the lengths (A+C) of the first and second holes 16 and 18 respectively of the blade 10.

It should be noted that the improved scalpel blade holder 30 of the present invention is a combination of two attachment mechanisms which each by itself would be inoperable for attaching the blade 10. By itself, if the slidable member 36 were not present, since the length of the support member 32 is less than the sum of the first and second lengths (A+C) of the first and second holes 16 and 18 of the blade 10 respectively, then the blade can move in the length direction and fall off the holder 30. Further, by itself, the slidable member 36 cannot hold the blade 10 because the blade 10 does not have a circular hole and can move in the length direction.

As for removal of the blade 10 from the improved blade handle 30 of the present invention, the health care worker simply pushes the slidable member 36 into the second position as shown in FIG. 4b. Since the slidable member 36 is no longer in the first hole 16 of the blade 10, the blade is no longer retained, and it can slide forward thereby slipping off the handle 30 with ease. In this manner, safety and health of the health care workers is greatly improved.

What is claimed is:

1. A scalpel blade holder for holding a scalpel blade having a blade portion near the anterior thereof and a blunt portion near the posterior thereof, a substantially elongated first hole near the blunt portion of said scalpel blade, said first hole having a first length and a first width with said first length being parallel to the direction from the anterior to the posterior; a substantially elongated second hole anterior to and coextensive with said first hole, said second hole having a second length parallel to and collinear with said first length, and a second width smaller than said first width, said holder comprising:
   an elongated handle member having a length, a width, and a thickness; said member having a distal end and a proximal end along said length;
   an elongated support member connected to said handle member and being an integral part thereof, near said distal end of said handle member; said support member having a groove along its periphery, parallel to said length direction, wherein the width of said support member between said groove is substantially equal to said second width of said blade, and wherein the length of said support member is less than the sum of said first and second lengths of said blade;
   a slidable member in said handle member, movable along said thickness direction, said slidable member having a width substantially equal to the first width of said blade and positioned in said handle member such that the distance from the proximal end of said slidable member to the groove at the distal end of said support member is substantially the same as the sum of said first and second lengths of said blade; and
   means for locking said slidable member in said thickness direction between a first position and a second position, wherein said first position said slidable member is above the plane of the groove, and in said second position said slidable member is just below the plane of the groove.

2. The blade holder of claim 1 wherein said slidable member is shaped substantially in a rod.

3. The blade holder of claim 2 wherein said rod has a groove.

4. The blade holder of claim 3 wherein said means for locking further comprises a retaining washer and a spring.

5. The blade holder of claim 4 wherein said spring is C shaped and is positioned in said groove of said rod.

6. The blade holder of claim 1 wherein said elongated support member is substantially elliptically shaped.

* * * * *